United States Patent
Domnich et al.

(10) Patent No.: US 11,992,296 B2
(45) Date of Patent: May 28, 2024

(54) TRANSPONDER SYSTEM AND METHOD FOR READOUT OF A PASSIVE TRANSPONDER

(71) Applicant: VesselSens GmbH, Bonn (DE)

(72) Inventors: Alexej Domnich, Bonn (DE); Fabian Tutsch, Cologne (DE)

(73) Assignee: VesselSens GmbH, Bonn (DE)

( * ) Notice: Subject to any disclaimer, the term of this patent is extended or adjusted under 35 U.S.C. 154(b) by 734 days.

(21) Appl. No.: 16/969,166

(22) PCT Filed: Feb. 15, 2019

(86) PCT No.: PCT/EP2019/053840
§ 371 (c)(1),
(2) Date: Aug. 11, 2020

(87) PCT Pub. No.: WO2019/158703
PCT Pub. Date: Aug. 22, 2019

(65) Prior Publication Data
US 2020/0367769 A1    Nov. 26, 2020

(30) Foreign Application Priority Data
Feb. 16, 2018    (DE) .................. 10 2018 202 430.8

(51) Int. Cl.
*A61B 5/0215* (2006.01)
*A61B 5/00* (2006.01)
(Continued)

(52) U.S. Cl.
CPC ........ *A61B 5/02158* (2013.01); *A61B 5/6852* (2013.01); *A61B 5/686* (2013.01);
(Continued)

(58) Field of Classification Search
CPC ... A61B 5/02158; A61B 5/6852; A61B 5/686; A61B 5/6862; A61B 5/6866;
(Continued)

(56) References Cited

U.S. PATENT DOCUMENTS 8,016,875 B2    9/2011  Philipp et al.
9,613,237 B2 *  4/2017  Nikunen ............ G06K 7/10158
(Continued)

FOREIGN PATENT DOCUMENTS

DE    196 19 311 C2    7/1998
DE    197 33 360 A1    2/1999
(Continued)

OTHER PUBLICATIONS

M/A-COM, "RF Directional Couplers and 3dB Hybrids Overview", M/A-COM, Jan. 15, 2016, retrieved from https://www.ieee.li/pdf/essay/directional_couplers.pdf (Year: 2016).*
(Continued)

*Primary Examiner* — Eric F Winakur
*Assistant Examiner* — Jonathan Drew Moroneso
(74) *Attorney, Agent, or Firm* — Leydig, Voit & Mayer, Ltd.

(57) ABSTRACT

The invention relates to a transponder system having at least one passive transponder, which has a resonant circuit having a variable resonant frequency, and having a readout device, wherein the readout device is designed to modify a frequency of the readout signal to the variable resonant frequency of the resonant circuit. The invention additionally relates to a method for readout of a passive transponder, which has a resonant circuit having a variable resonant frequency.

13 Claims, 5 Drawing Sheets

Figure 1:
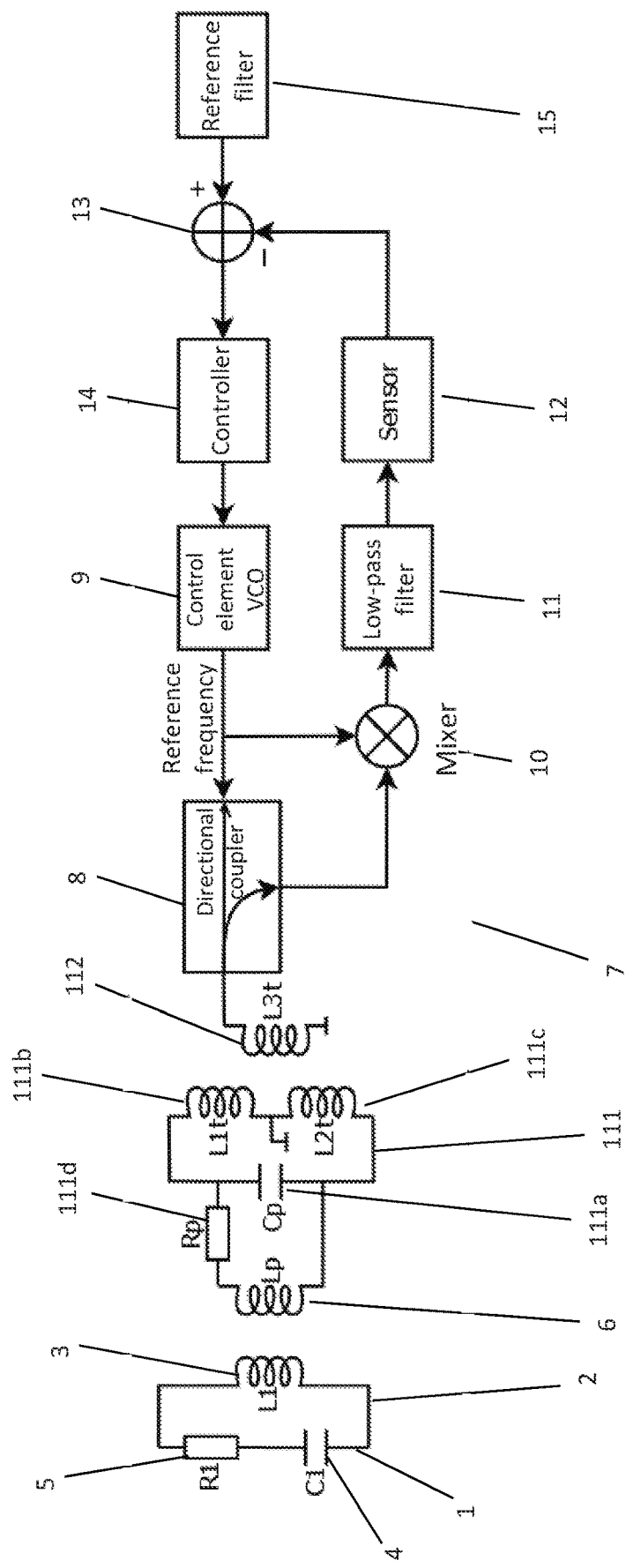

(51) Int. Cl.
*G01L 9/12* (2006.01)
*G06K 7/10* (2006.01)
*H04L 67/12* (2022.01)

(52) U.S. Cl.
CPC .......... *A61B 5/6862* (2013.01); *A61B 5/6866* (2013.01); *G01L 9/12* (2013.01); *G06K 7/10366* (2013.01); *H04L 67/12* (2013.01); *A61B 2562/0247* (2013.01)

(58) Field of Classification Search
CPC .......... A61B 2562/0247; A61B 5/7239; A61B 5/7242; A61B 2560/0219; A61B 5/0031; A61B 5/02108; G01L 9/12; G06K 7/10366; G06K 2007/10495; G06K 19/0719; G06K 7/10009; H04L 67/12
See application file for complete search history.

(56) References Cited

U.S. PATENT DOCUMENTS

| | | | | |
|---|---|---|---|---|
| 2006/0196277 | A1* | 9/2006 | Allen | G01R 23/12 73/861.12 |
| 2008/0281400 | A1 | 11/2008 | Philipp et al. | |
| 2014/0002111 | A1* | 1/2014 | Potyrailo | G01N 27/3278 29/832 |
| 2016/0310020 | A1* | 10/2016 | Warnking | A61B 5/6852 |
| 2017/0095667 | A1* | 4/2017 | Yakovlev | A61B 5/0022 |

FOREIGN PATENT DOCUMENTS

| | | | | |
|---|---|---|---|---|
| DE | 102011009695 | A1 | 8/2012 | |
| DE | 102011110252 | A1 | 12/2012 | |
| EP | 1 732 242 | A2 | 12/2006 | |
| EP | 1 854 406 | A1 | 11/2007 | |
| EP | 1 990 027 | A2 | 11/2008 | |
| WO | 2006/049796 | A2 | 5/2006 | |
| WO | WO-2012100959 | A1 * | 8/2012 | .......... A61B 5/0031 |
| WO | WO-2016005050 | A1 * | 1/2016 | .......... A61B 5/0031 |
| WO | WO-2018102435 | A1 * | 6/2018 | .......... A61B 5/0022 |

OTHER PUBLICATIONS

Think SRS, "About Lock-In Amplifiers", Think SRS, Nov. 1, 2011, retrieved from https://www.thinksrs.com/downloads/pdfs/applicationnotes/AboutLIAs.pdf (Year: 2011).*
Ziegler et al., "Optimum Settings for Automatic Controllers," *Transactions of the ASME* 64: 759-768 (1942).
German Patent Office, Office Action in German Patent Application No. 10 2018 202 430.8 (dated Dec. 18, 2018).
European Patent Office, International Search Report in International Application No. PCT/EP2019/053840 (dated May 29, 2019).
European Patent Office, Written Opinion in International Application No. PCT/EP2019/053840 (dated May 29, 2019).
International Bureau of WIPO, International Preliminary Report on Patentability in International Application No. PCT/EP2019/053840 (dated Aug. 18, 2020).
European Patent Office, Notification under Article 94 (3) EPC in European Patent Application No. 19 705 514.8 (dated Apr. 8, 2022).

* cited by examiner

TRANSPONDER SYSTEM AND METHOD FOR READOUT OF A PASSIVE TRANSPONDER

CROSS-REFERENCE TO RELATED APPLICATIONS

This patent application is the U.S. national phase of International Application No. PCT/EP2019/053840, filed on Feb. 15, 2019, which claims the benefit of German Patent Application No. 10 2018 202 430.8, filed Feb. 16, 2018, the disclosures of which are incorporated herein by reference in their entireties for all purposes.

The invention relates to a transponder system comprising at least one passive transponder which has a resonant circuit with a variable resonant frequency, and comprising a reading device, wherein the reading device is designed to match a frequency of the reading signal to the variable resonant frequency of the resonant circuit. The invention also relates to a method for reading a passive transponder which has a resonant circuit with a variable resonant frequency.

Passive transponders usually contain a resonant circuit which can be excited as a result of an alternating electromagnetic field being generated by means of a reading device, the frequency of said field being the resonant frequency of the transponder.

Such passive transponders can be used inter alia for monitoring tasks. In this case, the resonant frequency of the resonant circuit can be made dependent on an environmental state that is to be monitored. Such a dependence may be created for example by using sensors which change an inductance or a capacitance as a function of a variable that is to be monitored. If such a sensor is used in the resonant circuit of the passive transponder, the resonant frequency of the latter changes as a function of the value of the variable that is to be monitored. If an exciting alternating electromagnetic field is then applied to the passive transponder from outside, the occurrence of a resonance depends on whether the resonant frequency that is dependent on the value of the environmental state is equal to the resonant frequency of the excitation. If the resonance state is provided as the setpoint state, a deviation from the setpoint state can be recognized as a result of the fact that the resonant circuit of the transponder no longer resonates. In this way, the existence of the setpoint state can be monitored.

Such systems enable a decision as to whether the value measured by the sensor is or is not a setpoint value. If the system is in resonance, it can be deduced that the value has the setpoint value. If the system is out of resonance, it can be deduced that the value deviates from the setpoint value. However, the systems of the prior art do not permit continuous measurement of the value. The value is known only in the case where the value has the setpoint value. If the value to be measured by the sensor deviates from the setpoint value, therefore, it is unknown in the prior art.

It is an object of the present invention to specify a transponder system by which, in a passive transponder having a resonant circuit which has a varying resonant frequency, the varying resonant frequency can be determined. It is also an object to specify a method for reading a passive transponder, which method makes it possible, in a passive transponder with a varying resonant frequency, to determine this resonant frequency.

The object is achieved by the transponder system and by the method for reading a transponder described herein. Further advantageous developments of the transponder system according to the invention and of the method according to the invention for reading a passive transponder are also described.

According to the invention, a transponder system is specified which comprises at least one passive transponder. The passive transponder contains at least one resonant circuit which has a varying resonant frequency. The fact that the resonant frequency is varying can be understood to mean that the value of the resonant frequency varies over time, that is to say is temporally varying, when the transponder is used as intended. With particular preference, the resonant frequency varies continuously over time.

The transponder system according to the invention additionally comprises at least one reading device which has at least one reading inductance. A reading signal can be applied to the at least one resonant circuit of the passive transponder by means of the reading inductance. The reading signal may be an alternating electromagnetic field. According to the invention, the reading device is designed to match a frequency of the reading signal to the temporally variable resonant frequency of the resonant circuit. As a result, the reading device can continuously apply to the resonant circuit a reading signal which has a frequency equal to the resonant frequency of the resonant circuit at the time of application. If the resonant frequency of the resonant circuit changes, the reading device can match the frequency of the reading signal to the changed resonant frequency. Since the frequency of the reading signal is matched to the resonant frequency of the resonant circuit, the resonant frequency of the resonant circuit can be determined by means of the reading unit. In this way, therefore, the value of the resonant frequency can be determined for a varying resonant frequency of the resonant circuit of the transponder. It is advantageous if the frequency of the reading signal is continuously updated to the variable resonant frequency of the resonant circuit since this enables continuous knowledge of the resonant frequency.

In one advantageous embodiment of the invention, the resonant frequency of the resonant circuit may be variable in that an inductance or a capacitance of the resonant circuit can be adjusted by a measured value of the sensor. If the sensor value changes, the capacitance or inductance changes and thus the resonant frequency of the resonant circuit changes. Advantageously, therefore, at least one inductance together with at least one capacitive sensor, or at least one inductive sensor together with at least one capacitance, may be connected to form the at least one resonant circuit of the transponder. An embodiment in which a capacitive pressure sensor is connected to an inductance to form the resonant circuit is particularly advantageous. Capacitive sensors may have at least one capacitance or one capacitor. The capacitance can then change as a function of the pressure applied to the pressure sensor. One simple example of such a capacitive pressure sensor is a capacitor having two electrically conductive surfaces, the spacing of which depends on the ambient pressure. To this end, the two surfaces may be arranged for example on opposing surfaces of a housing that is closed in a pressure-tight manner.

The embodiment comprising at least one capacitive pressure sensor is particularly advantageous if the passive transponder is used for measuring the pressure of fluid, for example in a fluid conductor. The transponder system according to the invention then makes it possible to measure the pressure in the fluid line without having to make any intervention in the fluid line in order to carry out the measurement. Such a fluid line may be, for example, a blood vessel. In this case, it is particularly advantageous that the pressure can be measured without any intervention in the blood vessel.

In one advantageous embodiment of the invention, the reading device may have an excitation unit for generating a reading signal and a feedback unit for detecting a feedback signal coming from the passive transponder. The feedback unit may then be designed to transmit to the excitation unit a frequency matching signal which is determined on the basis of the feedback signal. The excitation unit can then match the frequency of the reading signal on the basis of the frequency matching signal. It is thus possible here to generate a reading signal which is applied to the passive transponder. As a result, a feedback signal comes from the passive transponder and is received by the reading device. If it is apparent from the feedback signal that the resonant frequency of the resonant circuit has changed, the frequency of the reading signal can accordingly be matched thereto. In this way, the frequency of the reading signal can be matched or updated to the resonant frequency of the resonant circuit.

To this end, the excitation unit may preferably have a signal source, by means of which the reading signal can be generated. The reading signal can be generated with a given frequency. Advantageously, the reading unit may additionally have a directional coupler, to the output of which the signal source is electrically coupled. The signal with the given frequency is therefore transmitted to the output of the signal source. The reading inductance can advantageously be electrically coupled to the input of the directional coupler. In this way, the signal with the given frequency that is generated by the signal source can be transmitted to the reading inductance and/or the signal reflected from the reading unit can be transmitted back to the input of the feedback unit.

In one advantageous embodiment of the invention, the feedback unit may have a mixer, by means of which a signal received by the reading inductance from the passive transponder can be mixed with or multiplied by the reading signal. In this way, the signal received by the reading inductance from the passive transponder can be filtered to the excitation frequency so that it is possible to determine any deviations, from the reading signal, of the frequency of the signal that is received from the passive transponder. Advantageously, the feedback unit may additionally have a low-pass filter, by means of which a signal output from the mixer can be filtered. As a result, high-frequency noise and other interfering signals can be filtered out. In particular, the feedback unit may advantageously be designed as a lock-in amplifier. The current value of the resonant frequency can in this case be fed back to the control loop and the frequency of the reading signal can be adjusted so that the deviation of the frequency of the reading signal can be reduced or eliminated.

The transponder system according to the invention can be used with particular advantage for measuring pressure in fluid lines. By measuring pressure in a fluid line, it is possible in particular to determine a speed of pulse waves in the fluid within the fluid line. To this end, the passive transponder may advantageously have at least two resonant circuits, which may be designed as described. In particular, the at least two resonant circuits may each have at least one capacitive pressure sensor as a capacitance. The passive transponder may therefore have a first resonant circuit with a first capacitive pressure sensor as capacitance and additionally a second resonant circuit with a second capacitive pressure sensor as capacitance. In this embodiment, the transponder system may then have a cylindrical device for the passage of fluid in the direction of a cylinder axis of the cylindrical device. The cylinder shape may be a circular cylinder shape in most cases, but it may also comprise any other cylinder shape. The fluid line may in particular also be a liquid line or a gas line.

Here, a fluid can be understood to mean a substance which offers no resistance to any slow shear, and which therefore has a finite viscosity. In particular, gases and liquids are fluids in this sense.

The capacitive pressure sensors of the at least two resonant circuits may then be arranged at different points of the cylindrical device along the cylinder axis. Therefore, the capacitive pressure sensor of the first resonant circuit may be arranged at a first point of the cylindrical device and the capacitance of the second resonant circuit may be arranged at a second point of the cylindrical device, said second point being at a distance from said first point along the cylinder axis. In this way, a pressure of the fluid can be measured at different points of the cylindrical device along the cylinder axis by means of the at least two capacitive pressure sensors. The cylindrical device may be, for example, a stent, an implant, a catheter and/or a fluid line, which may also be flexible.

Such an embodiment of the transponder makes it possible to measure the pressure in the cylindrical device at different points. As a result, it is possible in particular to determine a speed of pulse waves passing through the cylindrical device. A pulse wave leads to a temporal change in pressure at a given location along the cylinder axis. If the pressure is measured at different points, the pressure wave leads to a change in pressure at the different points one after the other. A time difference of the pressure change can be determined by means of the two resonant circuits, and then the pressure wave speed can be calculated from a known distance between the pressure sensors.

It has proven to be advantageous if, in the case where the passive transponder has a plurality of resonant circuits, said resonant circuits have resonant frequencies which differ from one another. As a result, the signals of the two resonant circuits can differ from one another when read. It is particularly advantageous if the resonant frequencies differ at least by such a magnitude that they do not superpose one another in such a way as to produce a beat. If, as described above, the resonant frequencies depend on measured values from one or more sensors, then the advantageous condition that the resonant frequencies do not superpose one another in such a way as to produce a beat is preferably met for all the measured values that are to be expected or that occur and thus for the associated resonant frequencies. If, therefore, the resonant circuits have for example capacitive pressure sensors as described above, then the resonant circuits are advantageously designed in such a way that their resonant frequencies, for all the pressures to be measured, do not superpose one another in such a way as to produce a beat.

The pressure sensors may advantageously be arranged at an equal distance from the cylinder axis. It is possible, but not essential, that the pressure sensors are arranged in the same direction as seen from the cylinder axis.

A method for reading a passive transponder is also according to the invention, wherein the passive transponder has at least one resonant circuit with a varying resonant frequency. A reading signal is applied to the at least one resonant circuit, and a frequency of the reading signal is matched to the varying resonant frequency of the resonant circuit. What has been stated above in relation to the passive transponder system applies to the method in a corresponding manner.

Advantageously, the frequency of the reading signal is continuously updated to the varying resonant frequency of the resonant circuit. The frequency therefore preferably makes no jumps. Preferably, the frequency of the reading signal is updated to the resonant frequency of the passive transponder by means of a control loop such that the frequency of the reading signal is precisely the respective current resonant frequency of the resonant circuit.

Advantageously, the method may be carried out by means of a lock-in amplifier. In this case, a feedback signal coming from the passive transponder can be received by the reading unit. The received feedback signal can then be fed to an input of a lock-in amplifier. A reference signal of the lock-in amplifier may in this case be the reading signal. The phase and amplitude of the feedback signal are obtained as the output of the lock-in amplifier. These can be fed to the control loop so that the frequency of the reading signal can be corrected on the basis of the magnitude or amplitude and the phase of the feedback signal. If the change in frequency is small in comparison to a bandwidth of the sensor resonance, then the phase signal can be used as an input variable for a setpoint value/actual value comparison in the control loop. Optionally, the phase signal and the amplitude signal, that is to say the complex signal as a whole, can be used to form a variable, by means of which control takes place. In this way, it is also possible to determine whether the deviation of the feedback signal from the reading signal is positive or negative. It is also possible to use the phase, wherein in this case advantageously a new function can be compiled from the phase and the derivation thereof, which enables an assessment as to how greatly the frequency deviates in the positive or negative direction (see FIG. 5). It is also possible to use the amplitude, wherein in this case then preferably also the derivation of the amplitude according to frequency is considered in order to be able to decide whether the deviation of the feedback signal from the reading signal is positive or negative. Alternatively, the phase and the amplitude can also be used in combination, so that the phase delivers, in particular, information about the sign of the deviation.

Advantageously, a relative pressure applied to the capacitive pressure sensor of the resonant circuit is determined from the frequency of the reading signal. According to the invention, it is not necessary that an absolute pressure value is determined; instead, it is sufficient to determine a relative pressure value which is related to a reference value. According to the invention, therefore, pressure differences in particular can be determined according to the invention.

Advantageously, the method according to the invention is carried out using a transponder system according to the invention as described above.

The invention will be explained below by way of example and with reference to some figures. Identical or corresponding features are denoted by identical reference signs. The features described in the examples may also be implemented independently of the specific example and may be combined among the examples.

Figure 2:
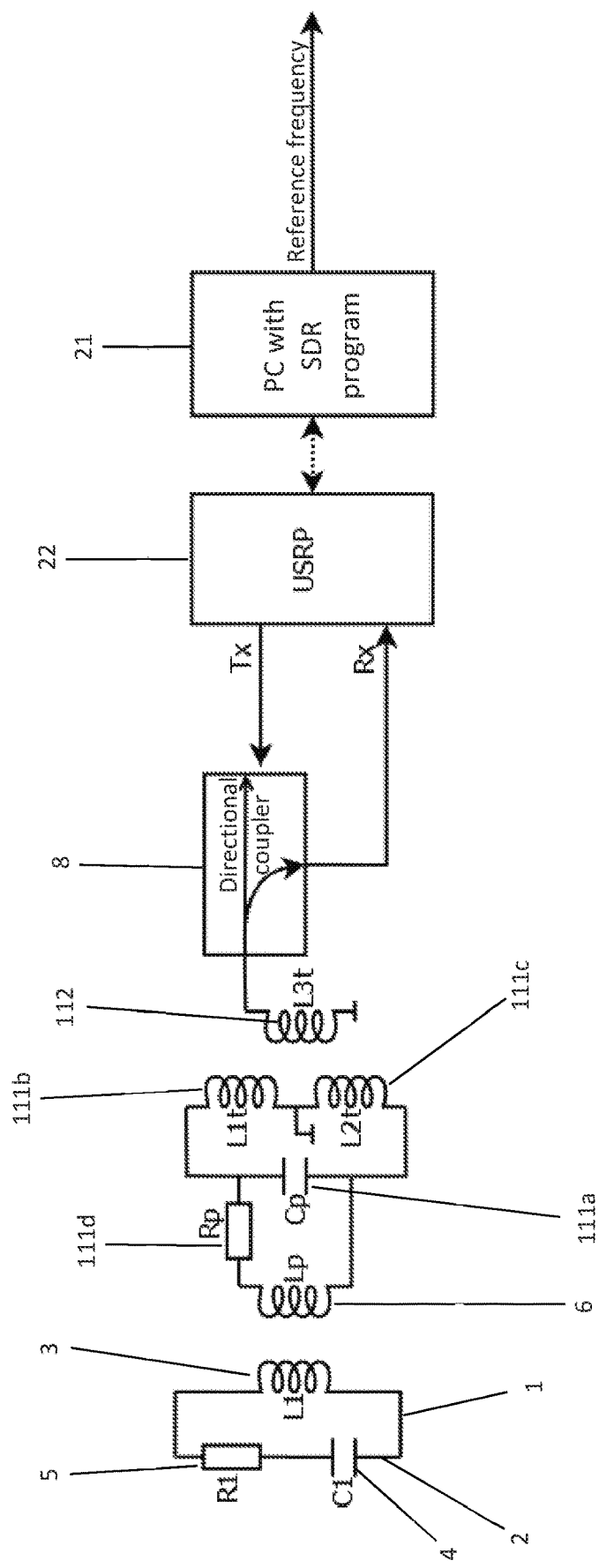
Figure 3:
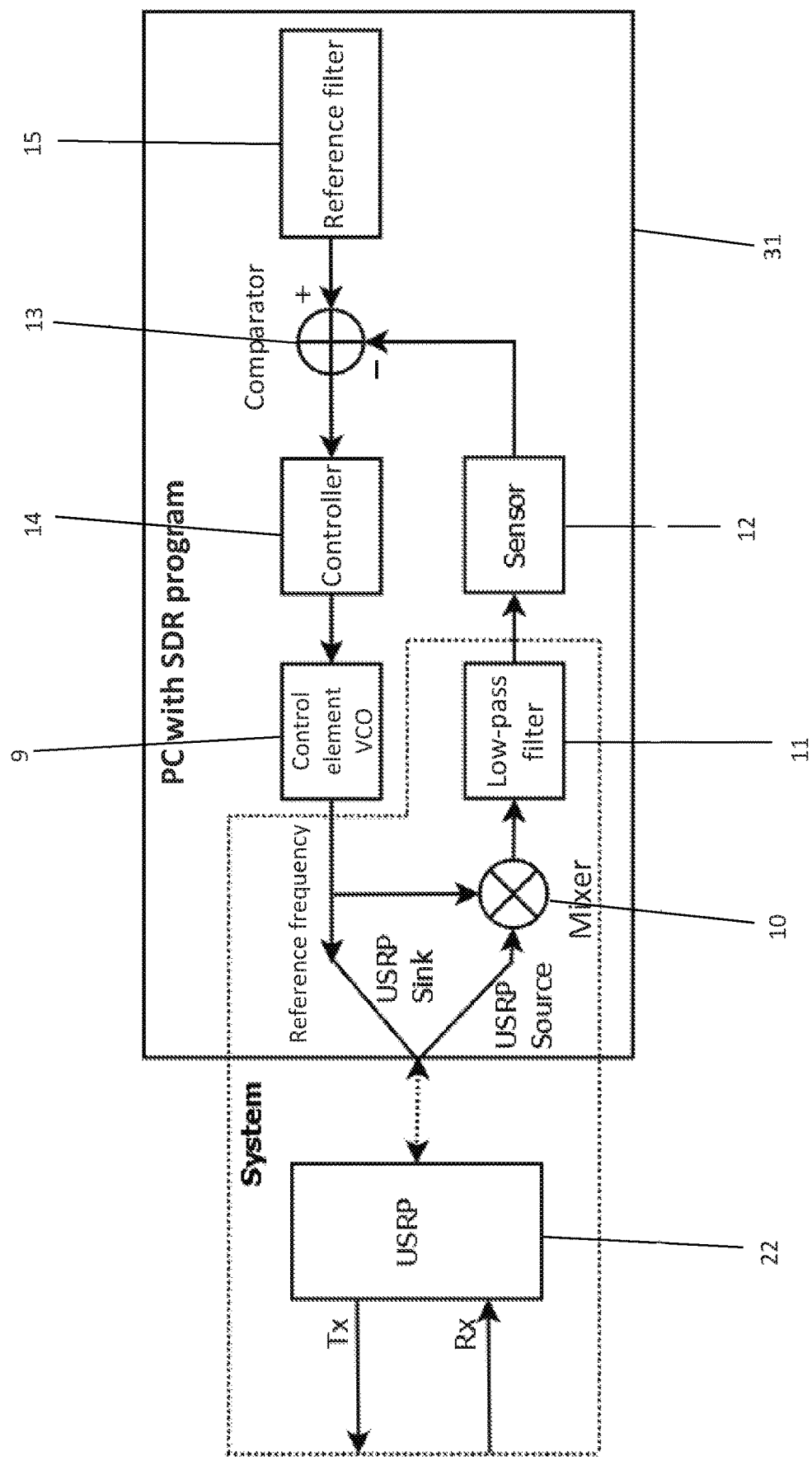
Figure 4:
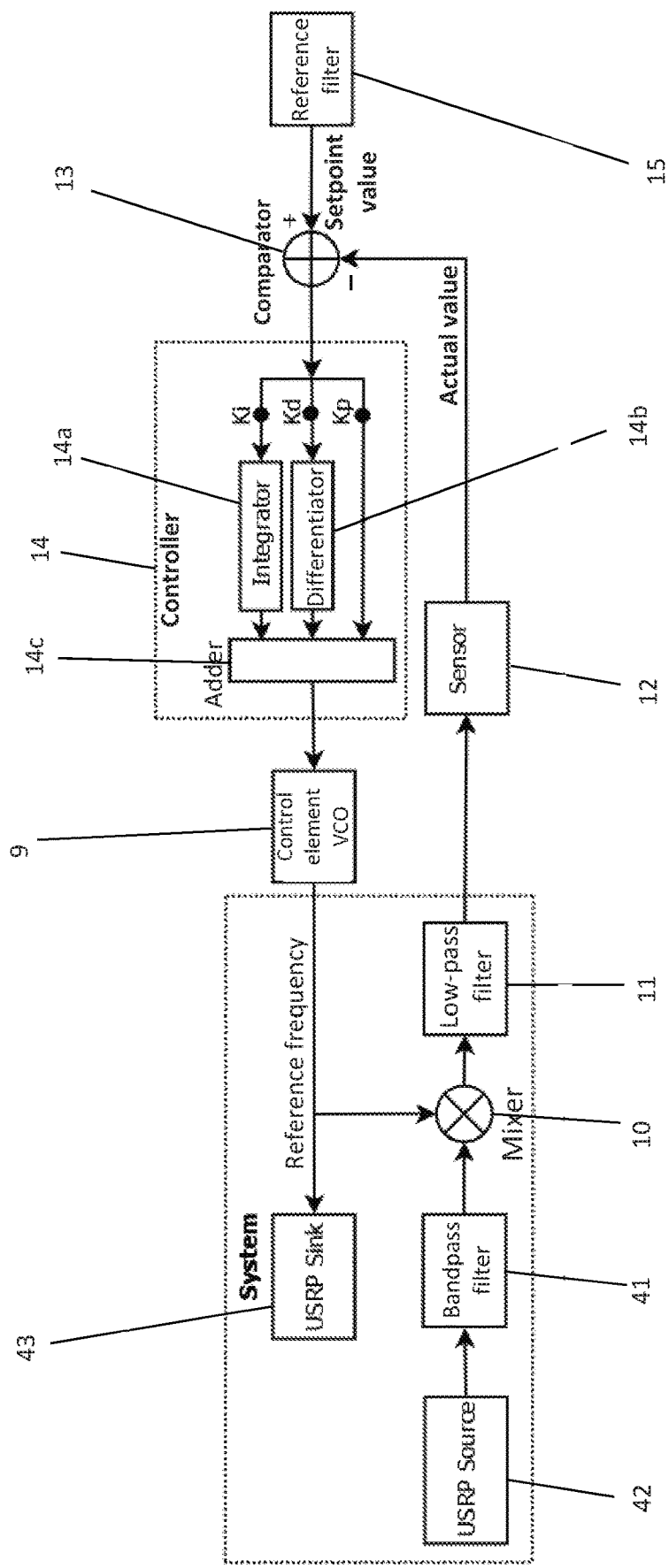
Figure 5:
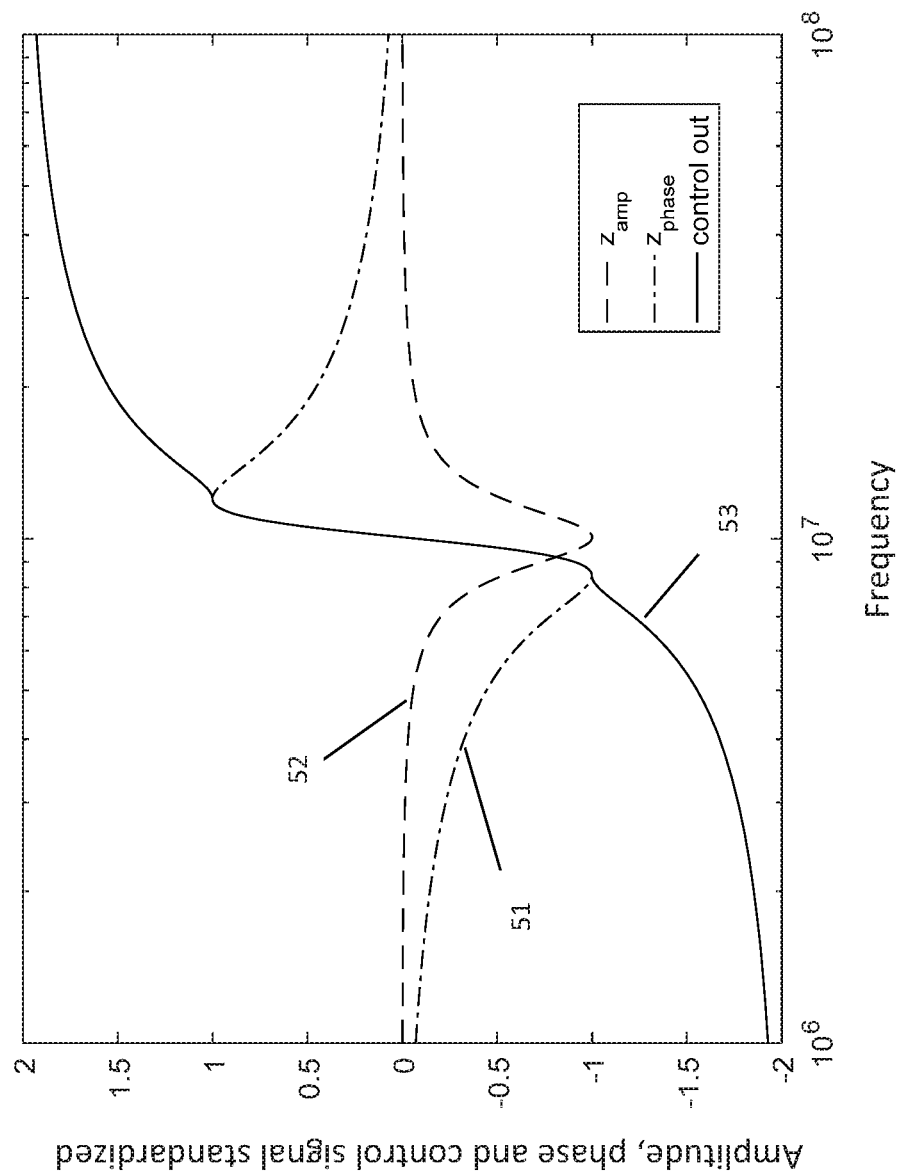

In the figures:

FIG. 1 shows a schematic block diagram of an exemplary transponder system according to the invention, FIG. 2 shows, in the form of a block diagram, an exemplary implementation of a transponder system according to the invention, FIG. 3 shows an exemplary implementation of a generation of a reading signal and of an evaluation of the feedback signal, as used in FIG. 2, in a control loop, FIG. 4 shows an exemplary implementation of the control loop shown in FIG. 3, FIG. 5 shows a diagram of phase and amplitude, as can be output from a lock-in amplifier as shown in FIGS. 3 and 4, and of a control signal derived from the phase and the derivation thereof.

FIG. 1 shows an example of a transponder system according to the invention, in the form of a schematic block diagram. The transponder system comprises a passive transponder 1 which contains a resonant circuit 2 with a varying resonant frequency. In the illustrated example, the resonant circuit 2 has an inductance 3 and a capacitance 4. A resistance 5 is also shown for the resonant circuit 2.

The transponder system shown in FIG. 1 additionally comprises a reading device 7 which contains a reading inductance 6. The reading inductance is connected here to an optional balun transmitter 111, which is able to convert the non-single-ended signal of the reading coil 6 (a symmetrical signal) into a single-ended signal. The signal generated by the balun transmitter 111 is then transmitted here to a secondary coil 112, which generates a signal that is fed into a single-ended input of a directional coupler 8. In the illustrated example, the reading coil has a parasitic capacitance 111a. A resistance 111d is shown between the reading coil 6 and the parallel connection of the parasitic capacitance 111a. Said resistance is the parasitic resistance of the reading coil. The inductances 111b and 111c are connected in parallel with the reading coil 6.

A signal source 9 for generating an alternating voltage signal with a predefined frequency is connected to one output of the directional coupler 8. Arranged at a second output of the directional coupler is a mixer 10 which mixes a signal entering the directional coupler 8 from the reading inductance 6 or the balun transmitter 111, and exiting through the second output, with the alternating voltage signal generated by the signal source 9. The signal output from the mixer 10 is fed to a low-pass filter 11, by means of which for example noise and interference components can be filtered out. The signal output from the low-pass filter can then be fed to a sensor 12, by means of which the amplitude and/or phase of the signal received from the reading coil 6 can be determined from the signal output from the low-pass filter 11. The sensor 12 may optionally also convert a complex signal that is output from the low-pass filter 11 into a real signal, which is then used for control purposes. The signal output from the sensor 12 can then be compared in a comparator 13 with a signal generated by a reference filter 15. If the change in frequency of the resonant circuits 2a, 2b is small in comparison to the bandwidth of the resonance of the resonant circuits 2a, 2b, then the phase signal is advantageously suitable as an input variable for the comparator 13. The signal output from the comparator 13 can then be fed to a controller 14, which outputs a frequency matching signal to the signal source 9 so that the frequency of the signal generated by the signal source 9 can be matched on the basis of the frequency matching signal output from the controller 14. In this way, the control loop shown in FIG. 1 makes it possible to match the frequency of the excitation signal generated by the signal source 9 to a changed resonant frequency of the resonant circuit 2. In the illustrated example, the signal source 9 is a voltage-controlled oscillator which generates a signal with a frequency that is dependent on the applied voltage, here generated by the controller 14.

If the passive transponder 1 has only one resonant circuit 2, the signal source 9 for reading the resonant circuits may generate one single sine signal with a given frequency. If the passive transponder 1 optionally has a plurality of resonant circuits 2, these may advantageously have frequencies that differ from one another. In this case, the signal source 9 may advantageously generate a signal in which a number of sine functions corresponding to the number of different resonant circuits are superposed with the different frequencies of the plurality of resonant circuits. The different frequencies can be read by means of the reading coil 6. Preferably, the signal output from the directional coupler 8 to the mixer 10 is in this case mixed separately with the sine signals having the different resonant frequencies. To this end, advantageously a corresponding number of separate mixers 10 may be provided. The separate signals thus generated can then be fed in each case to a low-pass filter 11 and a sensor 12, which in each case determines the amplitude and/or phase for all components. Separate feedback to the signal source 9 may then take place for all frequency components. Therefore, in the case where the passive transponder 1 has a plurality of resonant circuits 2 with different resonant frequencies, preferably a separate mixer 10, a separate low-pass filter 11, a separate sensor 12, a separate comparator 13, a separate controller 14 and a separate reference filter 15 and a separate control element 9 are provided for each of the resonant frequencies. An adder may additionally be provided, which superposes the signals generated by the control elements and outputs these jointly to the directional coupler 8. An embodiment with two resonant circuits 2 is particularly advantageous, since this makes it possible to measure pressure wave speeds.

FIG. 2 shows, by way of example, a block diagram of an implementation of the control loop in FIG. 1 for reading a transponder 1 which has one resonant circuit 2. The resonant circuit 2, the balun transmitter 111, the reading coil 6 and the directional coupler 8 are designed as shown in FIG. 1. Reference should therefore be made to the description relating to FIG. 1. The mixer 10, the low-pass filter 11, the sensor 12, the comparator 13, the reference filter 15, the controller 14 and the control element 9 are in this example implemented in a computer 21, which is connected to the directional coupler 8 via a Universal Software Radio Peripheral (USRP) 22. However, said elements may also be implemented as individual digital components or as analogue circuits, which would lead to the block diagram shown in FIG. 1. The USRP 22 transmits a reference signal Tx to one output of the directional coupler 8 and receives a feedback signal Rx from the other output of the directional coupler 8.

FIG. 3 schematically shows an implementation of a circuit 31 for evaluating the signal output from the USRP 22. The circuit 31 may be connected to the USRP 22 by means of a USB connection for example. The feedback signal Rx is fed to the mixer 10 via a USRP source. The control element 9 feeds the reading signal Tx to the USRP 22 via a USRP sink. The mixer 10, the low-pass filter 11, the sensor 12, the comparator 13, the reference filter 15, the controller 14 and the control element 9 are connected as shown in FIG. 9, and therefore reference should be made to the associated description. Said elements are embodied here as objects of an item of software, but they may also be embodied as individual digital components or as analogue components.

FIG. 4 shows the embodiment of the invention shown in FIG. 3, with a detailed view of the controller 14 and with a bandpass filter 41 downstream of the USPR source 42. Here, the signal output from the USRP source 42 is first fed to the bandpass filter 41, which allows the passage of, for example, only frequencies around a given mid-frequency and removes frequencies higher than an upper cutoff frequency and/or lower than a lower cutoff frequency. The signal output from the bandpass filter 41 is then fed to the mixer 10.

In the example shown in FIG. 4, the controller 14 has an integrator 14a, which integrates the signal output from the comparator 13 over time. The controller 14 additionally has a differentiator 14b, which calculates a derivation of the signal output from the comparator over time.

In the controller 14, the signal output from the comparator is fed to the integrator 14a and to the differentiator 14b. In an adder 14c, the signal output from the comparator is added to the signal output from the integrator 14a and from the differentiator 14b, and a voltage is obtained as a result of the addition, said voltage being used to control the voltage-controlled oscillator 9. The signal output from the comparator 13 may optionally be multiplied in each case by a constant value before being introduced into the integrator 14a, the differentiator 14b and the adder 14c. In FIG. 4, the signal introduced into the integrator 14a may be multiplied by a value Ki, that signal introduced into the differentiator may be multiplied by a value Kd, and the signal fed directly to the adder 14c may be multiplied by a value Kp.

The constants Ki, Kd and Kp may be adapted to the system that is to be controlled. Via said constants, the controller can be set in such a way that the controller and the system as a whole behave in a stable manner. To this end, an optimum should be found between control speed and accuracy. By way of example, for this purpose, the step response of the system is determined in an open-loop configuration. To this end, a step function was applied to the system as a whole, which is shown in FIG. 3, at the input of the control element 9. The controller 14 was removed and the circuit was thus interrupted at this point. The step response can then be measured at the output of the comparator 13. Based on the step response, a suitable parameter combination for Ki, Kd and Kp can be found for example by using the Ziegler and Nichols method (Ziegler, J. G.; Nichols, N. B.: Optimum settings for automatic controllers, Trans. ASME, 64 (1942), pp. 759-768).

Since the controller 14 monitors the signal and the signal source 9 or control element 9 continuously delivers in the form of a voltage value the frequency that is currently to be set, this can also be tapped off at that point, that is to say between the controller 14 and the control element 9 in FIG. 4).

FIG. 5 shows, by way of example, a curve of a phase 51, of an amplitude 52 and of a control signal 53, as can be generated by the sensor 12 in FIGS. 1 to 4. The centre point of the diagram is, in the frequency direction (horizontal direction), the excitation frequency that is fed in and, in the vertical direction, a zero point of a standardized phase, amplitude and control signal. Around the zero point in the centre of the diagram, the phase signal has a linear region in which the deviation of the feedback signal from the reading signal can be deduced directly from the phase. The amplitude is symmetrical in the frequency of the reading signal so that, for control purposes, use should be made of additional information indicating the direction in which the feedback signal deviates from the reading signal. This may be, for example, the phase or else a derivation of the amplitude according to frequency, the sign of which depends on the sign of the deviation. While the phase signal is particularly suitable for small frequency deviations, the deviation in the control signal can be determined over a wide range of frequency deviations.

The control signal may be generated, for example, in the manner described below. Use of the control signal is advantageous because it clearly defines, over the entire range of frequency deviations, whether the actual resonant frequency is below or above the excitation frequency. It is particularly advantageous in the case of resonant frequency changes of more than f(min(z_phase)) to f(max(z_phase)).

Since this is a real-time signal processing using a signal that repeats with the pulse frequency (for example approximately 70 Hz), it is possible for example in a first step to determine over one or more periods the parameters (for example phase minimum z_phase_min and phase maximum z_phase_max) which can be used to generate the control variable control_out. In the second step, the real-time processing can then take place using the parameters previously obtained. It would also be possible to obtain the parameters adaptively in real time.

In one exemplary embodiment, in which the control variable is determined from the phase, use may be made for example of the following sequence, which is reproduced here as pseudo-code:

```
% determination of the parameters from the measured data of
one or more periods between two times t_min and t_max)
z_phase_min = min(z_phase(t_min:t_max))
z_phase_max = max(z_phase(t_min:t_max))
% continuous processing of the data at the sampling instants i
z_phase_d(i) = diff(z_phase(i));
if z_phase_d(i)<=0 && z_phase(i)<=0 % Region 0
    control_out(i) = 2*z_phase_min - z_phase(i);
elseif z_phase_d(i)>0 % Region 1
    control_out(i) = z_phase(i);
elseif z_phase_d(i)<=0 && z_phase(i)>=0 % Region 2
    control_out(i) = 2* z_phase_max - z_phase(i);
else% error
    control_out(i) = nan;
end
```

Here, z_phase is the phase, z_phase_d is the derivation of the phase, and control_out is the value of the control signal.

The invention can measure, for example, the pressure changing over time in blood vessels. To this end, the resonant circuit 2 together with a capacitive pressure sensor 4 and a coil 3, which at the same time is used for coupling to the reading coil 6, can be introduced into the blood vessel so that it is exposed therein to the pressure changing over time. Via a reading coil 6 which is inductively coupled extracorporeally, an excitation frequency, which is the resonant frequency of the sensor at a given pressure, can then be fed in and the feedback can be observed. By means of the invention, advantageously all occurring pressures over time can be measured, so that continuous measurement of the pressure is possible. As a result, it is also possible to determine, with greater accuracy, variables which can be determined from one or more pressures, such as a pulse wave speed for example. Since a larger portion of the pressure curve can be measured, more data points can be determined and therefore the pulse wave speed can be determined with a greater degree of accuracy than when using only a trigger pressure.

The invention may be embodied as an analogue circuit or by means of digital signal processing, for example as an SDR with frequency conversion or as an analogue/digital converter with a DA converter without frequency conversion. The invention can be used with advantage in all applications in which inductive coupling is used between sensors, in particular implanted sensors, and a reading unit. In this way, periodic or non-periodic signals can be detected with particular advantage.

The invention claimed is:

1. A transponder system comprising at least one passive transponder, wherein the passive transponder has at least one resonant circuit with a varying resonant frequency, and at least one reading device, wherein the reading device has at least one reading inductance, wherein a reading signal can be applied to the at least one resonant circuit by means of the reading inductance, and wherein the reading device is configured to match a frequency of the reading signal to the varying resonant frequency of the resonant circuit,
   wherein the reading device has an excitation unit for generating the reading signal and a feedback unit for detecting a feedback signal coming from the passive transponder,
   wherein the feedback unit is designed to transmit to the excitation unit a frequency matching signal which is determined on the basis of the feedback signal,
   wherein the excitation unit is designed to match the frequency of the reading signal on the basis of the frequency matching signal,
   wherein the excitation unit has a signal source, by means of which the reading signal can be generated, and
   wherein the reading device additionally has a directional coupler, to the output of which the signal source is electrically coupled and to the input of which the reading inductance is electrically coupled.

2. The transponder system according to claim 1, wherein the reading device is designed to continuously update the frequency of the reading signal to the varying resonant frequency of the resonant circuit by means of a control loop, wherein the feedback unit together with the excitation unit forms the control loop.

3. The transponder system according to claim 1, wherein the feedback unit has a mixer, wherein a signal received by the reading inductance from the passive transponder can be mixed with or multiplied by the reading signal by means of the mixer.

4. The transponder system according to claim 3, wherein the feedback unit additionally has a low-pass filter, by means of which a signal output from the mixer can be filtered.

5. The transponder system according to claim 1, wherein at least one inductance and at least one capacitive sensor or at least one inductive sensor and at least one capacitance are connected to form the at least one resonant circuit.

6. The transponder system according to claim 1, wherein the passive transponder has at least two of the resonant circuits, wherein the at least two resonant circuits each has at least one capacitive pressure sensor as capacitance,
   further comprising a cylindrical device for the passage of fluid in the direction of a cylinder axis of the cylindrical device, wherein the capacitive pressure sensors of the at least two resonant circuits are arranged at different points of the cylindrical device along the cylinder axis, and a pressure of the fluid can be measured at the different points by means of the two capacitive pressure sensors.

7. The transponder system according to claim 6, wherein the resonant circuits have different resonant frequencies which differ such that they do not superpose one another in such a way as to produce a beat.

8. The transponder system according to claim 6, wherein the cylindrical device is a stent, an implant, a catheter and/or a fluid line.

9. A method for reading a passive transponder in a transponder system according to claim 1, the method comprising matching the frequency of the reading signal to the varying resonant frequency of the resonant circuit.

10. The method according to claim 9, wherein the frequency of the reading signal is continuously updated to the varying resonant frequency of the resonant circuit.

11. The method according to claim 9, wherein the frequency of the reading signal is updated by means of a control loop such that the frequency of the reading signal is the respective present resonant frequency of the resonant circuit.

12. The method according to claim 9, wherein a feedback signal coming from the passive transponder is received, and the feedback signal is fed to an input of a lock-in amplifier, wherein a reference signal of the lock-in amplifier is the reading signal.

13. The method according to claim 9, wherein a relative pressure is determined from the frequency of the reading signal which is applied to a pressure sensor acting as the capacitance of the resonant circuit.

* * * * *